United States Patent [19]

Bailey et al.

[11] Patent Number: 5,013,240
[45] Date of Patent: May 7, 1991

[54] PORTABLE DENTAL APPARATUS

[75] Inventors: James R. Bailey, Indianapolis; C. Robert Schrock, Greenwood, both of Ind.

[73] Assignee: International Equipment & Supply Corp., Indianapolis, Ind.

[21] Appl. No.: 540,084

[22] Filed: Jun. 19, 1990

[51] Int. Cl.$^5$ .................. A61G 15/00; A61C 1/02
[52] U.S. Cl. .................. 433/77; 433/98; 433/79
[58] Field of Search .................. 433/98, 99, 101, 77, 433/79

[56] References Cited

U.S. PATENT DOCUMENTS

| 3,081,542 | 3/1963 | Sherfey | 433/101 |
| 4,160,323 | 7/1979 | Tracy | 433/77 |
| 4,217,009 | 8/1980 | Suter | 312/209 |

FOREIGN PATENT DOCUMENTS

| 0094470 | 11/1983 | France | 433/98 |
| 1251915 | 1/1971 | United Kingdom | 433/77 |
| 2165760 | 4/1986 | United Kingdom | 433/77 |

Primary Examiner—John J. Wilson
Assistant Examiner—Cindy A. Cherichetti
Attorney, Agent, or Firm—Woodard, Emhardt, Naughton, Moriarty & McNett

[57] ABSTRACT

A portable dental apparatus. A main housing includes a plurality of wheels mounted therebeneath. A control panel on the main housing includes a variety of controls for operating a plurality of dental tools removably and suspendedly mounted to a holder in turn movably mounted to the main housing. A storage cavity formed in the housing allows storage of the holder and tools when the portable dental apparatus is in a transport state. The tools are connected by a plurality of lines to a plurality of drive and power components located in the interior of the main housing. A lid hingedly mounted atop the control panel may be opened revealing the controls for the tools. An X-ray display screen and amalgamator are provided respectively on the lid and control panel.

8 Claims, 7 Drawing Sheets

PORTABLE DENTAL APPARATUS

BACKGROUND OF THE INVENTION

This invention is in the field of dental tools.

DESCRIPTION OF THE PRIOR ART

A number of conventional dental tools including high and low speed drills, syringe and suction devices, and light curing wands are utilized in the delivery of dental services. These tools are powered by electric components including a compressor, a vacuum pump and light source. Traditional tools including X-ray view screens and amalgamators are also required in the practice of dentistry. In the standard dental office, the aforementioned tools are removably mounted to a heavy stationary post, and are further connected to various electric and fluid lines to various sources of power. As such, it is necessary for the patient to visit the permanent dental site to facilitate receiving dental services. It can be appreciated that in many cases the visit to the dental office is of great inconvenience and in certain instances impossible for the patient.

We have designed a portable dental apparatus allowing the dentist to perform the various dental services at the residence or other close location to the patient. Such a portable dental apparatus is particularly convenient when the patient is in the hospital or rest home or when located at a temporary field installation such as found in the military.

SUMMARY OF THE INVENTION

One embodiment of the present invention is a portable dental apparatus comprising a portable main housing having an interior, a transport device beneath the main housing operable to allow the portable dental apparatus to have an in-use stationary state and a transport state, a dental tool holder means on the main housing, a plurality of dental tools removably mountable on the dental tool holder, a driver mounted within the interior operable to drive the dental tools, a connector connected between the driver and the plurality of dental tools, and, a lid mounted to the main housing, the lid and the main housing forming a storage cavity to receive the plurality of dental tools and the connector when the portable dental apparatus is in the transport state.

It is an object of the present invention to provide a portable dental apparatus.

A further object of the present invention is to provide a portable means for transporting a plurality of dental tools in a ready to use condition.

A further object of the present invention is to provide a portable dental apparatus having means for storing dental tools when in a transport state with the tools extendable therefrom when in an in-use stationary state.

Related objects and advantages of the present invention will be apparent from the following description.

DESCRIPTION OF THE PREFERRED EMBODIMENTS

Figure 1:
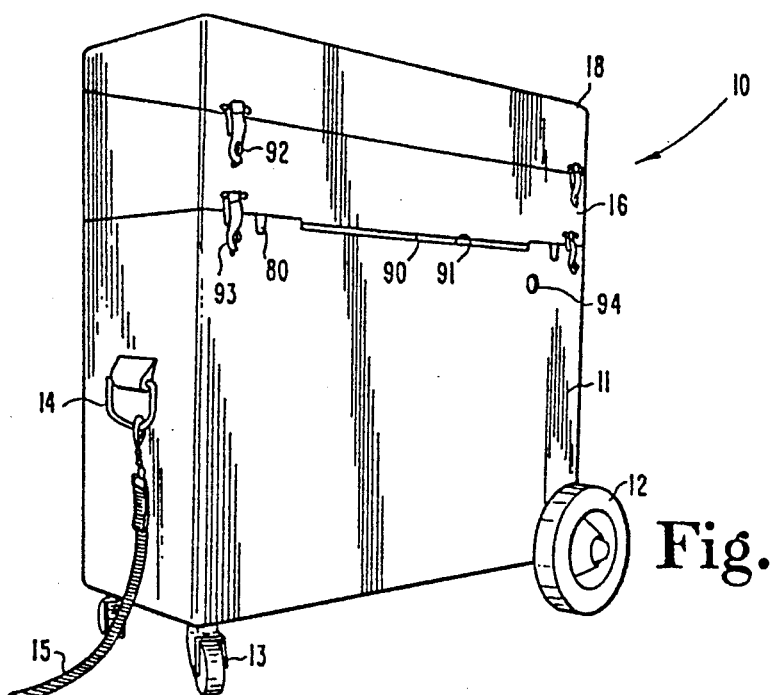
FIG. 1 is a perspective view of an alternate embodiment of the portable dental apparatus incorporating the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown an alternate embodiment of the portable dental apparatus incorporating the present invention. Portable dental apparatus 10 having a portable main housing 11 mounted atop a pair of conventional rear, oversized wheels 12 and a pair of front castor wheels 13. A pair of conventional handles 14 are mounted to the opposite ends of housing 11 with the front handle being removably attached to a pulling strap 15. Wheels 12 and 13 provide a transport means located beneath the main housing which is operable to allow the portable dental apparatus to have an in-use stationary state when strap 15 is not pulled forwardly and a transport state when the strap is pulled to the patient site.

A control panel 16 is hingedly mounted atop main housing 11 by a conventional hinge 17 (FIG. 2) extending longitudinally along one edge of the control panel and main housing. Likewise, a lid 18 is hingedly mounted atop control panel 16 also by means of a conventional hinge 19 (FIG. 3) secured to the adjacent longitudinally extending edge of the control panel and lid.

Figure 2:
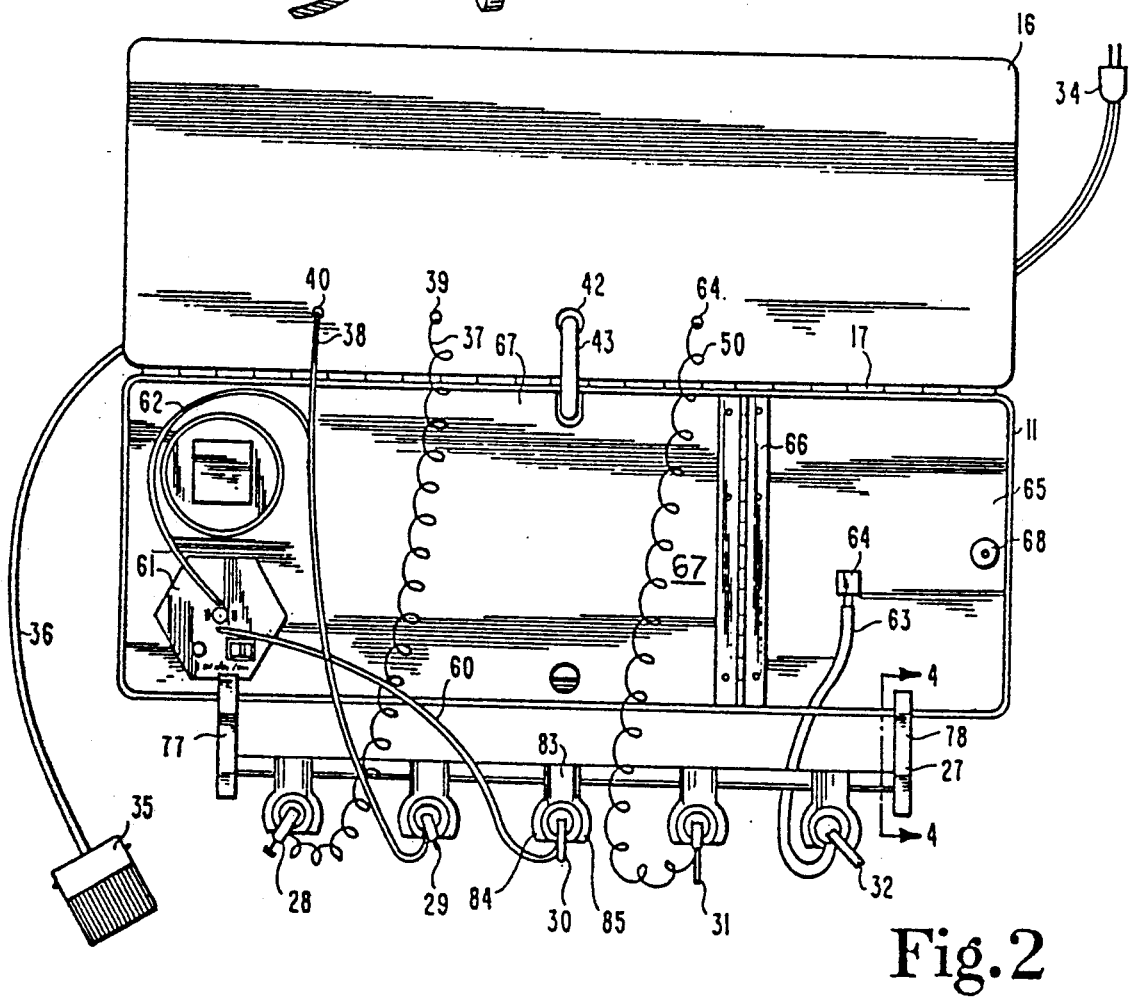
FIG. 2 is a top view of the apparatus of FIG. 1 with the control panel open displaying the various dental tools.
Figure 4:
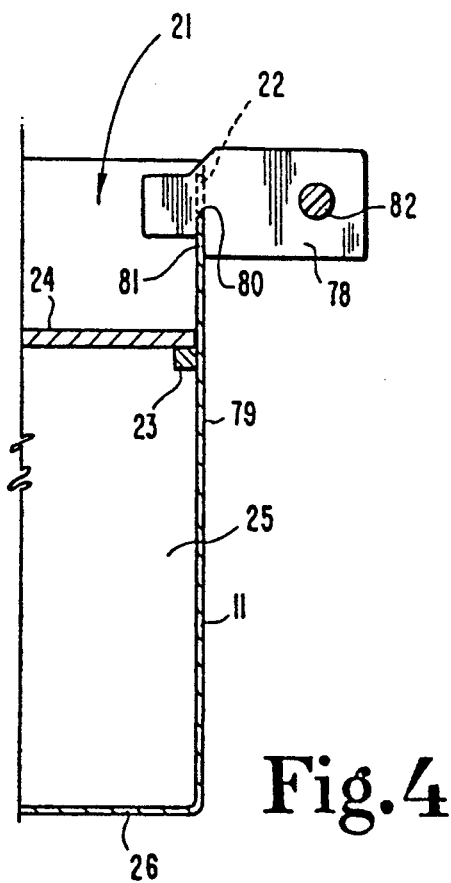
FIG. 4 is an enlarged cross-sectional view taken along a line and viewed in the direction of arrows 4—4 of FIG. 2.

Main housing 11 is a five-sided box having an open top when the control panel 16 is swung to the open position as depicted in FIG. 2. A storage cavity 21 (FIG. 4) is formed in the upper portion of main housing 11 by means of a removable horizontally extending wall 24 which rests atop a pair of flanges 23 extending inwardly from the parallel longitudinally extending vertical side walls of main housing 11. A number of components are mounted within the interior 25 of main housing 11 formed between the main housing bottom wall 26 and the removable storage cavity bottom wall 24. Storage cavity 21 extends from removable wall 24 up to the top edge 22 of the vertical side and vertical end walls of main housing 11.

A plurality of dental tools are stored within storage cavity 21 when the portable dental apparatus is in the transport state, but are removable therefrom when the portable dental apparatus is in an in-use stationary state. Likewise, a tool holder 27 (FIG. 2) is stored within cavity 21 when the portable dental apparatus is in the transport state, but is removable therefrom and mountable upon edge 22 to suspendedly and removably hold the plurality of dental tools. The dental tools shown in the embodiment depicted in the drawings include a low speed drill hand piece 28 (FIG. 2), a high speed drill hand piece 29, a light curing wand 30, a three-way syringe 31 and a suction hand piece 32. Such dental tools are commercially available and may be purchased for example from the following sources:

| Drill hand piece | Lares Research Company, 1581 Industrial Road, San Carlos, California 94070 |
| Light curing wand | Lares Research Company, 1581 Industrial Road, San Carlos, California 94070 |
| Three-way syringe | Marus Dental International, 20554 Builder Street, Bend, Oregon 97701 |

Fixedly mounted within interior 25 of main housing 11 is an electric air compressor 33 (FIG. 5) connectable to a source of electrical energy by a conventional line 34 (FIG. 1). Compressor 33 is commercially available from Gast Manufacturing Corp., Benton Harbor, Mich. 49022 under Model No. ROA-P 108-GB. Line 34 extends through the back vertical side wall of the main housing, but is removable therefrom for storage within cavity 21 when the portable dental apparatus is in a transport state. Likewise, a conventional foot pedal 35 (FIG. 1) is connected by a conventional electric line 36 extending through the back vertical side wall of the main housing and is removable therefrom for storage within cavity 21 when the portable dental apparatus is in the transport state. Both lines 34 and 36 are operably connected to compressor 33 not only to provide power to the compressor, but allow the operator to activate and increase the speed of the compressor or to deactivate the compressor. The compressed air output line of compressor 33 is operably connected to lines 37 and 38 (FIG. 2) connected respectively to hand pieces 28 and 29 to power the drill bit on each hand piece. Both compressed air lines 37 and 38 are connected at their outer ends respectively to hand pieces 28 and 29 and extend respectively through apertures 39 and 40 to toggle switch 41 (FIG. 3) mounted to control panel 16. Toggle switch 41 is conventional i nature and has two positions, either to route the compressed air to the high speed drill hand piece or the low speed drill hand piece. A compressed air tube is operably connected between high speed/low speed toggle switch 41 and a second conventional two-way toggle switch 55 in turn connected via combination line 43 (FIG. 2) extending out of control panel 16 via hole 42 to the compressed air output of compressor 33. Switch 55 is operable to direct the compressed air either to syringe 31 or the high or low speed drill hand pieces 28 and 29, depending upon the position of switch 41. Conventional pressure gage 44 is operably connected to switch 55 to provide an indication of the air pressure therein at the switch.

Figure 5:
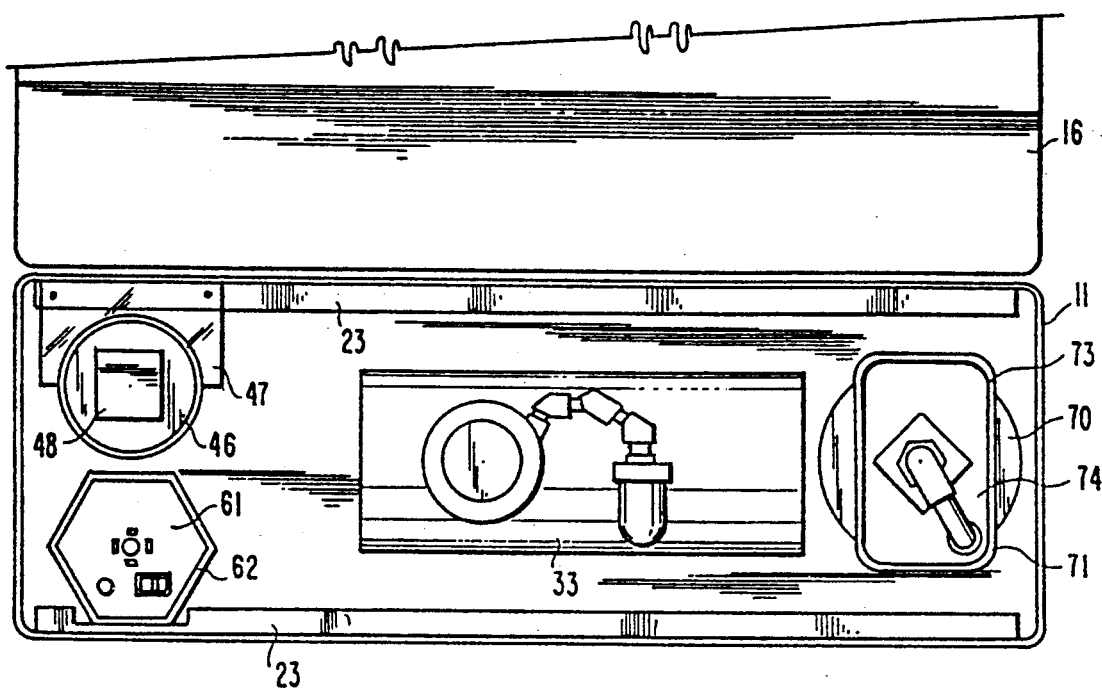
FIG. 5 is the same view as FIG. 2 only showing the tools and the bottom wall of the storage cavity removed to depict the components within the main housing interior.

High speed drill hand piece 29 has means for emitting water and thus line 38 includes a water conduit therein which is connected to a two-way water on/off toggle switch 45 in turn connected by a water conduit to a water volume adjust switch 49. A water conduit extends from water adjust switch 49 via combination line 43 to the reservoir 46 (FIG. 5). Compressor 33 is operable to pressurize reservoir 46 and force water outwardly therefrom depending upon the positions of the toggle switches. Reservoir 46 is mounted within housing 11 by bracket 47 and has a removable top 48 to facilitate filling of the reservoir with water.

Syringe 31 is operable to emit either compressed air or water depending upon the operation of the controls located on the syringe. Syringe 31 is connected via line 50 which has a compressed air conduit and a water conduit therein. The compressed air conduit is connected to the hand piece/syringe toggle switch 55 which is operable to direct compressed air to the syringe hand piece. Line 50 extends through aperture 64 into control panel 16 with the water conduit therein connected to reservoir 46.

The light curing wand 30 is connected via fiber optic line 60 to a conventional source of light 61 located within a bracket fixedly mounted within the interior of main housing 11. Such a light source is available from Lares Research Company, 1581 Industrial Road, San Carlos, Calif. 94070, under Model No. Quartz Fire SX. A separate fiber optic line 62 extends from source 61 through line 38 to the high speed drill hand piece 29 providing illumination.

A conventional suction hand piece 32 is connected via conduit 63 to a fitting 64 mounted atop door 65 pivotally mounted by conventional hinge 66 to wall 67. Door 65 and wall 67 comprise the bottom wall 24 of the storage cavity. A knob 68 is mounted to door 65 to allow access into the interior of the main housing without removing wall 67. A conventional vacuum pump 70 (FIG. 5) is mounted within the interior of the main housing and is located beneath door 65. Removably mounted atop vacuum pump 70 is a container 71 for catching and holding liquid removed via suction tool 32. Vacuum pump 70 is connected to a source of electrical energy and includes a on-off knob 72 mounted to the face of control panel 16. The combination pump and container is conventional in nature and commercially available. The top continuous edge 73 of container 71 sealingly engages the downwardly facing surface of door 65 having a gasket thereon. Fitting 64 extends through door 65 and opens into the container cavity 74 formed by edge 73. Pump 70 is operable to apply a withdrawal pressure within cavity 74 and thus through fitting 64 to suction tool 32 via conduit 63. Container 70 is removable from pump 70 once door 65 is open to facilitate the emptying of the container.

Figure 6:
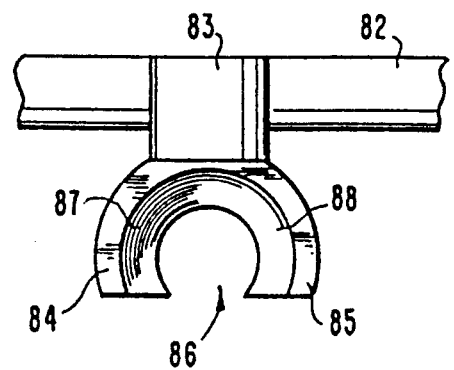
FIG. 6 is an enlarged top view of a tool holder.

The tools are removably held by holder 27 having a pair of ears 77 and 78 (FIG. 2) which mount within notches provided on the front vertically extending side wall of the main housing. Ear 78 will now be described, it being understood that a similar description applies to ear 77. Front side wall 79 (FIG. 4) includes a notch 80 received in a downwardly opening slot 81 provided on the inwardly positioned end of ear 78. A horizontally extending rod 82 is fixedly secured to and extends between ears 77 and 78 and has five (5) commercially available tool holders 83 fixedly mounted thereon each for holding one the five previously described tools. Holders 83, as well as the various tubing and switches shown in the drawings, are available from Marus Dental International, 20554 Builders Street, Bend, Oreg. 97701. Each tool holder 83 has a pair of outwardly extending arms 84 and 85 (FIG. 6) with the distal ends of the arms spaced apart to form an opening 86 through which the tool may be extended. Arms 84 and 85 have upwardly sloping surfaces 87 and 88 which extend convergingly downward to restrict downward movement of the tool. Thus, the small end of the tool is inserted through slot 86, the tool then being extended downwardly until it rests atop surfaces 87 and 88.

Figure 3:
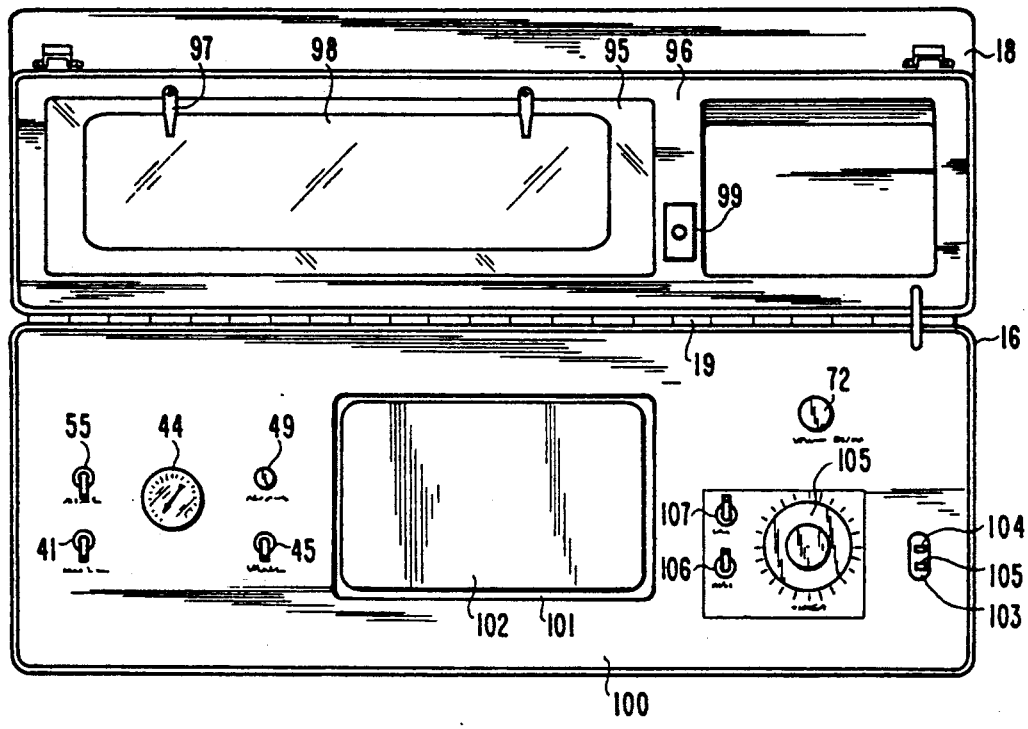
FIG. 3 is the same view as FIG. 1 only showing the lid open depicting the various controls for the dental tools of FIG. 2.

The top edge 22 (FIG. 4) of the vertically extending front side wall 79 extends downwardly forming recess 91 (FIG. 1) and opening 90 into storage cavity 21 to allow lines 37, 38, 60 and 50 to extend outwardly even though control panel 16 is closed. When the portable dental apparatus is in a transport state, lid 18 is latched in the closed position atop control panel 16 by conventional fastening devices 92. Likewise, in the transport state, the control panel 16 is in the closed position and is latched to the main housing 11 by conventional fastening devices 93. In the transport state, holder 27 along with tools 28 through 32, lines 37 and 38, 60, 50 and 63, power line 34 and line 36 with pedal 35 are all positioned within storage cavity 21 with the control panel and lid latched in the closed position. On the other hand, when the portable dental apparatus is in the in-use stationary position, holder 27 is mounted to the front side wall and extends outwardly as depicted in FIG. 2 with the five tools 28 through 32 mounted thereon. Lines 37, 38, 50 and 60 extend through opening 90 from the storage cavity 21 wherein they are connected as previously described. Control panel 16 is therefore latched in the closed position as depicted in FIG. 1 with lines 37, 38, 60 and 50 extending through opening 90 over bar 82 to tools 28 through 31 mounted within holders 83. Likewise, suction tool 32 is mounted to the holder with conduit 63 extending rearwardly through aperture 94 (FIG. 1) to fitting 64 located within the storage cavity. While in the in-use stationary position, lid 18 is open as depicted in FIG. 3.

A lightable X-ray display screen 95 is provided on surface 96 of lid 18 and has a pair of clips 97 for releasably holding an X-ray film 98. Suitable lighting devices are located behind screen 95 with power being routed thereto by a conventional on/off switch 99 in turn connected to a source of electrical energy via line 34. Surface 100 of control panel 16 is recessed in the central portion 101 to removably receive a container 102 for holding various supplies. A conventional amalgamator 103 is mounted to surface 100 of control panel 16 having a pair of upwardly extending arms 104 and 105 for releasably receiving a container of materials to be shaken. Conventional controls including a timer 105, a mull toggle switch 106, and a high/low speed toggle switch 107 are mounted to the control panel and are operably connected between the amalgamator and the source of electrical energy to control the speed and duration of the shaking motion.

The preferred embodiment of the portable dental apparatus is shown in FIGS. 7-11. A portable dental apparatus 110 (FIG. 7) is similar to the portable dental apparatus 10 previous described; however, the cabinet is structured differently and the number of tools and tool holder are different along with the components for powering the tools. Apparatus 110 has a main housing 111 mounted atop four conventional wheels 112 each being rotatable to allow the apparatus to be moved across a horizontal surface. Each wheel is pivotably mounted about a vertical shaft 113 allowing each wheel to pivot facilitating ease of movement. Further, each front wheel includes a brake handle 115 which may be moved downwardly thereby locking the wheel and preventing rotation of the wheel.

Figure 8:
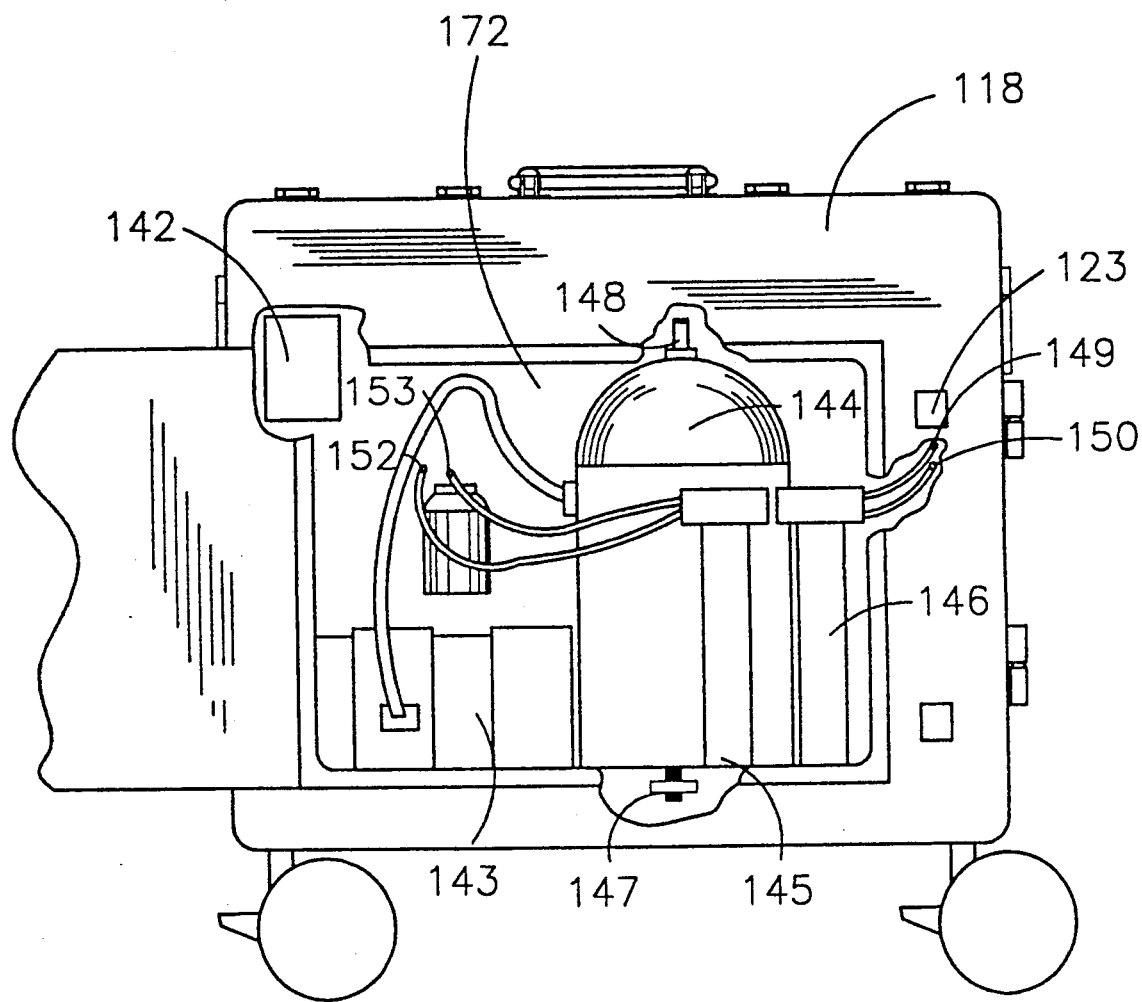
FIG. 8 is a back view of the apparatus of FIG. 7 with the rear access door open displaying the various drive components.

Main housing 111 includes a pair of end walls 116 integrally joined to a lower front wall 117 and a rear wall 118 (FIG. 8). Likewise, the end walls, lower front wall and rear wall are integrally joined to a bottom wall having wheels 112 rotatably mounted thereto. A recessed handle 119 is formed in each end wall 116.

Figure 7:
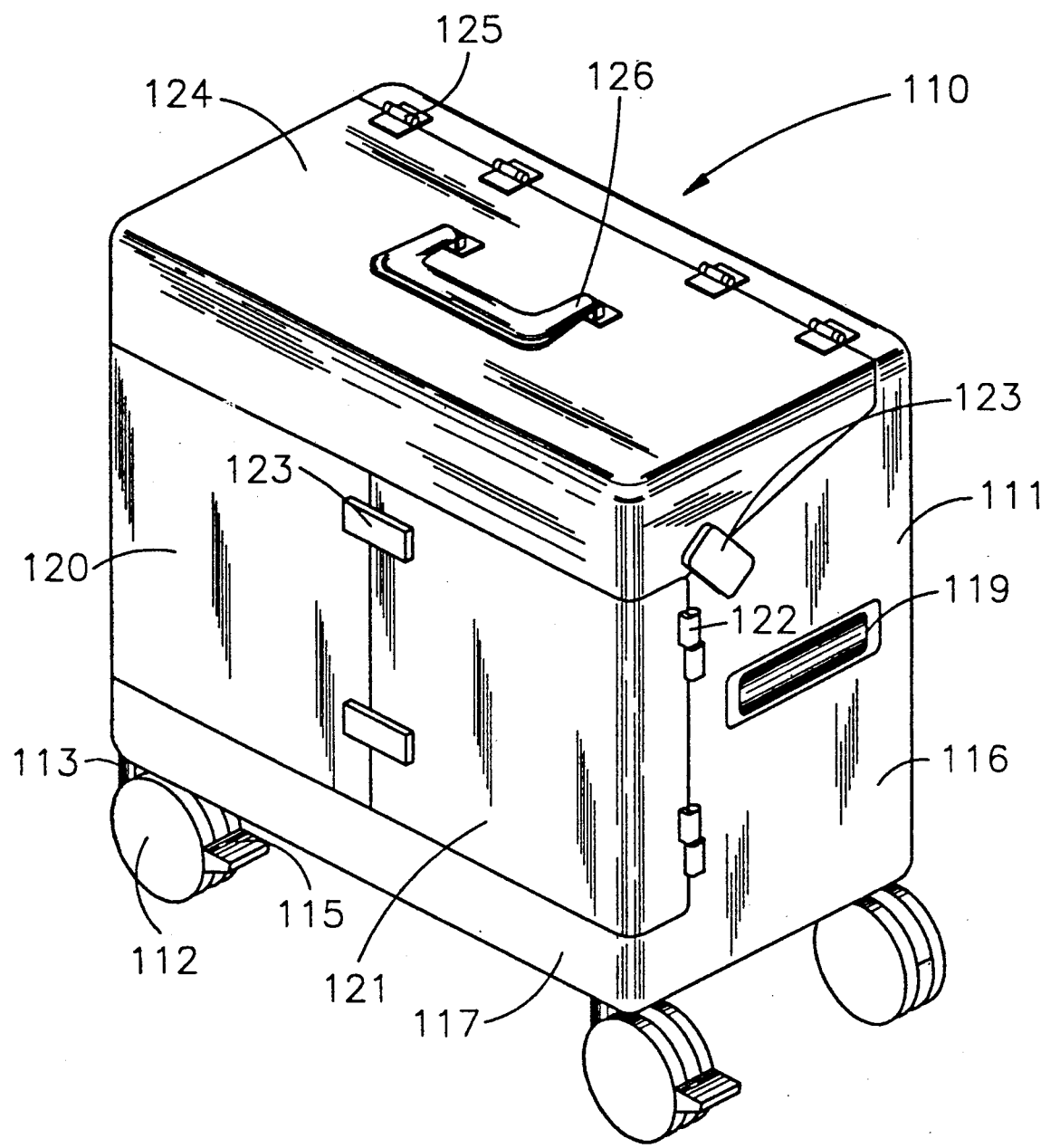
FIG. 7 is a perspective view of the preferred embodiment of the portable dental apparatus incorporating the present invention.

A pair of front doors 120 and 121 have opposite ends pivotably mounted by conventional hinges 122 to the end walls of the main housing. Hinges 122 are conventional lift off hinges so that the door may be easily removed. Doors 120 and 121 are shown in FIG. 7 in a closed position with the mutually facing vertically extending edges of the doors in contact and secured together by a pair of clasps 123. Clasps 123 are conventional in design and are mounted to door 121 being operable to releasably engage a mating component mounted to door 120. By releasing clasps 123 the doors may be pivoted about hinges 122 to the open position revealing the various tools mounted within the main housing. A lid 124 is pivotably mounted by a plurality of conventional hinges 125 in turn secured to main housing 111. A handle 126 is provided on the upper surface of lid 124 to facilitate lifting of the portable dental apparatus. Likewise, an additional pair of clasps 123 are mounted to the opposite end walls 116 of the main housing and are operable to releasably engage complimentary components provided on the downwardly extending skirt of lid 124. By opening the clasps, lid 124 may be pivoted to the open position. With the front doors and lid open as shown in FIG. 9, there are depicted six tools 128 through 133 removably mounted to a tool holder 127.

Tool holder 127 is similar to the tool holder 27 described with the alternate embodiment with the exception that holder 127 is slidably mounted to the front of the housing and is non removable therefrom and with the further exception that a total of eight tools may be mounted to the holder. In the embodiment shown in FIG. 9, six tools are shown mounted to the holder with two spare mounting recesses being provided for additional tools. Tool holder 127 (FIG. 10) has a holder main body 183 fixedly mounted to a pair of rearwardly extending arms 184 and 185 in turn slidably mounted to a recessed front wall 186 of the main housing. The rearwardly extending arms have a T-shaped configuration each of which is received in a T-shaped recess 187 provided in the recessed front wall 186 (FIG. 11). Arms 184 may be hollow to allow wires connected between the micro-switches within recesses 198 to extend to the power supply within the housing. The tools have been removed from the view in FIG. 10 to illustrate the tool holder recesses 196 which are identical to the recesses shown in FIG. 6 for the alternate embodiment. That is, each recess 196 includes a narrow mouth through which the tool may be inserted with the upwardly facing surfaces being concave or sloped downwardly surrounding each recess 196 to support the enlarged head of each tool. The recessed front wall 186 of main housing 111 is spaced a sufficient distance rearward of the lower front wall 117 of the main housing to allow arms 184 and 185 to be extended completely into the housing thereby positioning holder 127 along with the tools mounted thereto between vertical planes defined by walls 117 and 186. Doors 120 and 121 may then be pivoted closed so as to be vertically aligned with the lower front wall 117 thereby forming a tool storage area 197. Further, lower front wall 117 extends upwardly from the bottom wall 198 of the main housing forming a storage cavity into which various air lines, electrical cords and a foot pedal may be temporarily stored.

Figure 9:
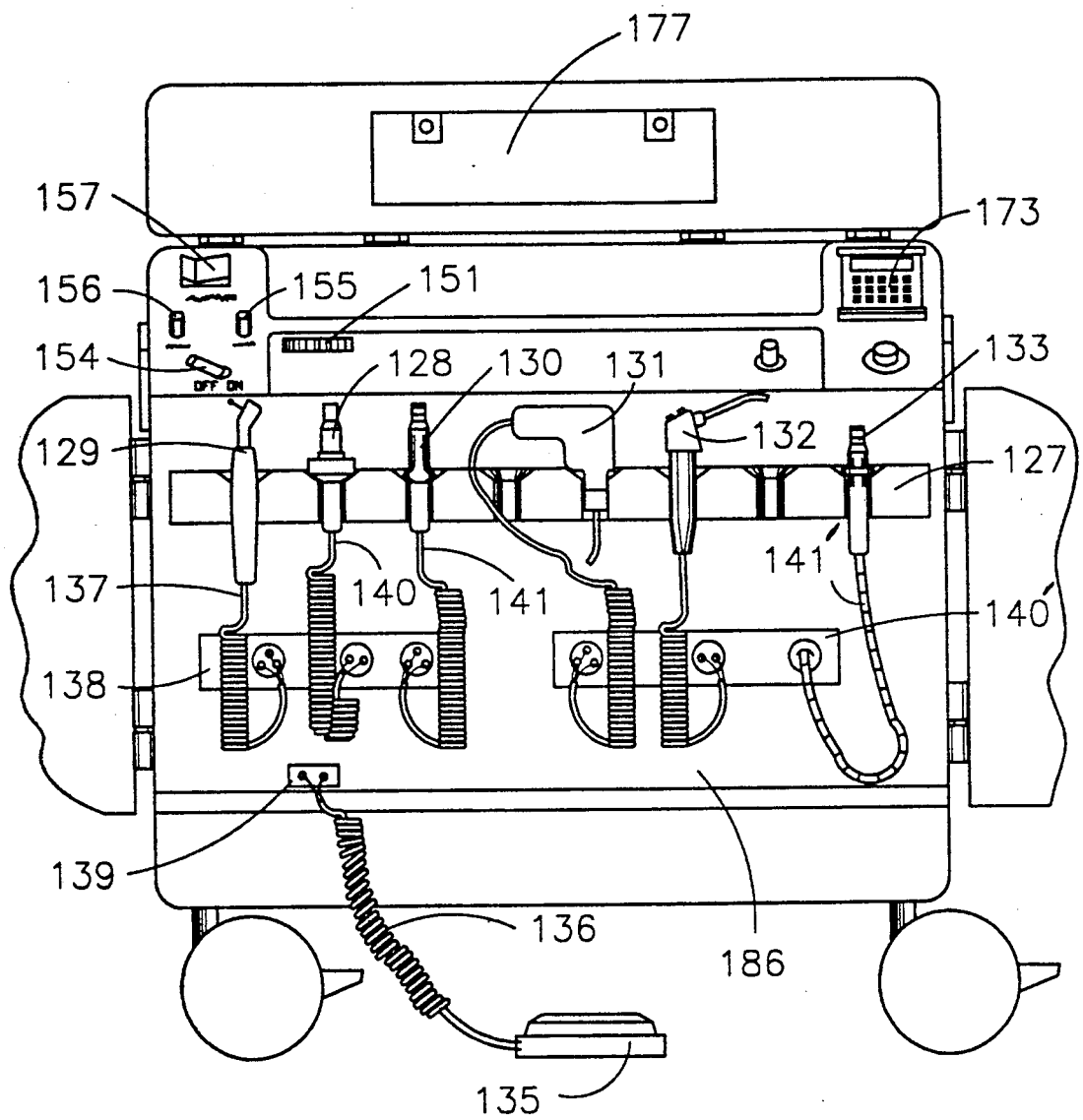
FIG. 9 is a fragmentary front view of the apparatus of FIG. 7 only showing the lid and front doors open depicting the various controls and tools.
Figures 10, 11:
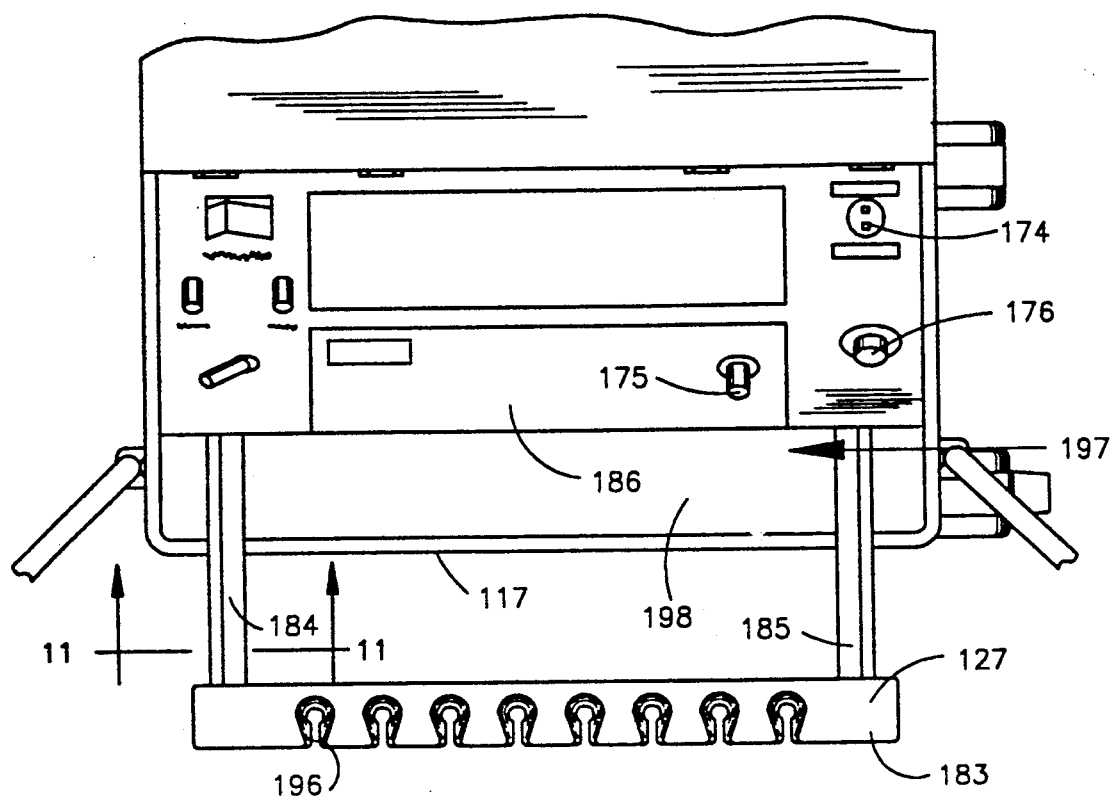
FIG. 10 is a fragmentary top view of the apparatus of FIG. 7.
FIG. 11 is an enlarged cross-sectional view taken along a line and viewed in the direction of arrows 11—11 of FIG. 10.

A high speed drill hand piece 129 identical to hand piece 29 is removably mounted to the first tool holder recess as viewed from left to right in FIG. 9. In the next tool holder recess is removably mounted a low speed drill hand piece 128 identical to the low speed drill hand piece 28 previously described. Removably mounted to the drill tool holder adjacent low speed drill hand piece 128 is a ultrasonic air scaler 130. In the embodiment shown in FIG. 9, the fourth drill holder recess as viewed from left to right is empty and is provided for an additional tool which is not disclosed herein. In the fifth tool holder recess is removably mounted a light curing unit 131 whereas in the next tool recess is removably mounted a three-way syringe 132 identical to the three-way syringe 31 previously described. Light curing unit 131 is distinguishable from the light curing wand 30 previously disclosed in that a source of light is provided within light curing unit 131 whereas tool 30 was connected by fiber optics to a source of light energy within the main housing of the portable dental apparatus. Light curing unit 130 is commercially available from Demetrol Research Corporation, 5 Ye Olde Road, Danberry, Conn. 06810. The second from the right tool recess as viewed in FIG. 9 is left empty for an additional tool not shown in the drawing whereas the tool recess formed at the right end of tool holder 127 removably holds a vacuum tube 133.

The high speed drill hand piece 129 has an output rotatable at approximately 300,000 revolutions per minute. The commercially available tool is also provided with a water spray outlet and a light source. Thus, three separate lines are included within line 137 and are connected to and extend between tool 129 and three connectors mounted to connector plate 138 provided on the recessed front wall 186. A foot pedal control 135 connected via line 136 to control plate 139 is operable to control the air volume to the three air controlled hand pieces including tool 129. The low speed hand piece 128 is provided with a water spray outlet but does not include a light source. Thus, tool 128 is connected via line 140 to a pair of connectors provided on plate 138. The commercially available low speed hand piece has an output rotatable at approximately 20,000 revolutions per minute. The ultrasonic air scaler 130 has both a vibratory air outlet and water outlet and is connected via line 141 to three outlets provided on plate 138. Pedal 135 is operable to control the volume of air delivered to each tool 128 and 129 and 130. The ultrasonic air scaler is commercially available under designation Titan SW Scaler from Star Dental Product, 1816 Colonial Village Lane, Lancaster, Penna. 17601. The light curing tool 131 and three-way syringe 132 are connected respectively to an electric outlet and a pair of outlets provided on plate 140' mounted to the recessed front wall 186 of the main housing. Last, the suction tool 133 is connected via a suction hose 141' to a vacuum connector provided on plate 140'.

The tools are connected via the aforementioned lines to various power sources located within the main housing. A rear door is hingedly mounted to the back wall 118 of the main housing and includes a pair of clasps 123 which releasably hold the door in the closed position. The door is shown fragmented and in the open position in FIG. 8 illustrating the interior 172 for holding an electric power supply 142, air compressor 143, an air holding tank 144, a waste water reservoir tank 145 and a fresh water reservoir tank 146. Air compressor 143 is electrically connected to a conventional electric power supply 142 in turn having an electric line extending outwardly from the main housing to a source of electrical energy. Compressor 143 is operable to pressurized air holding tank 144 which is provided with suitable valves for safety purposes and for maintaining the air within the tank at a predetermined level. Outlet valve 147 is mounted to the bottom of tank 144 and extends outwardly through the bottom wall of main housing 111 to allow tank 144 to be drained for maintenance purposes. Air holding tank 144 is connected through foot pedal 135 and pressure gage 151 (FIG. 9) mounted to the front of the main housing. The air line is then connected to an air manifold in turn connected to three air outlets provided on connector plate 138 each of which is connected to lines 137, 140, and 141 of the high speed drill piece 129, low speed drill piece 128, and ultrasonic air scaler 130. The foot pedal 135 is operable to control the volume of air delivered to the three pneumatic tools 128-130.

Compressor 143 is also connected via a filter to the waste water reservoir tank 145 via conduit 152. A second conduit 153 is connected to tank 145 and suction hose 141' via plate 140'.

The fresh water is provided by fresh water reservoir tank 146 having a first conduit 149 connected to the outlet 148 of air holding tank 144 thereby pressurizing the water within tank 146. The outlet conduit 150 of tank 146 is connected via an on-off toggle valve 154 (FIG. 9) and water volume control valve 155 to a water manifold. The water manifold in turn is connected via plate 138 (FIG. 9) to a separate water outlet for each line 137, 140, and 141 providing water spray capability to tools 128 through 130. The fresh water reservoir tank is also connected via plate 140' to the three-way syringe 132. The syringe is also connected via air volume control valve 156 to the air holding tank 144. An on-off switch 157 controls operation of the primary electrical system. Thus, switch 157 controls operation of the compressor and controls current flow to the power supply and thus all controls.

A countdown electronic timer 173 is removably mounted to the top of the main housing beneath lid 124. The battery operated timer is slidably mounted to a pair of rails secured to the housing and may be removed therefrom revealing a conventional amalgamator 174 (FIG. 10) identical to the amalgamator 103 previously described. A high-low amalgamator toggle switch 175 and a amalgamator timer 176 are provided on the recessed front wall 186 of the main housing. The amalgamator has a pair of upwardly extending arms for releasably receiving a container of materials to be shaken. The high-low switch 175 and on-off timer 176 are operably connected between the amalgamator and the source of electrical energy to control the speed and duration of the shaking motion. A lightable X-ray display screen 177 is provided on the inside surface of lid 124 and has a pair of clips for releasably holding an X-ray film.

Several of the tools are provided with automatic on-off switches located within the holder recess. Such a switch is found for example within recess 196 (FIG. 10) of tool holder 127 corresponding to the recesses holding tools 128, 129, 130, and 133. The switch takes the form of a spring biased projection which extends into recess 196. When the tool is not mounted to the tool holder the projection extends to the most forward position within the recess thereby turning the tool to the on position. Once the tool is mounted to the tool holder 127 and extends into recess 196 then the tool will contact and depress the micro switch thereby deactivating the tool.

The portable dental apparatus disclosed herein is totally self contained. Once the apparatus is connected to a source of electrical energy, the tools are immediately operational without requiring any set-up procedures. The preferred embodiment is particularly advantageous in that the tool holder is slidably mounted to the main housing eliminating the need for tool set-up.

While the invention has been illustrated and described in detail in the drawings and foregoing description, the same is to be considered as illustrative and not restrictive in character, it being understood that only the preferred and alternate embodiments have been shown and described and that all changes and modifications that come within the spirit of the invention are desired to be protected.

What is claimed is:

1. A portable dental apparatus comprising:
a portable main housing having an interior, said main housing including transport means therebeneath operable to allow said portable dental apparatus to have an in-use stationary state and a transport state;
dental tool holding means on said main housing;
a plurality of dental tools removably mountable on said dental tool holding means;
drive means mounted within said interior operable to drive said dental tools;
connecting means connected between said drive means and said plurality of dental tools;
a control panel operably associated with said drive means and said plurality of dental tools, said control panel located on said main housing with said main housing sized to form a storage cavity to receive said plurality of dental tools and said connecting means when said portable dental apparatus is in said transport state;
said dental tool holding means is movably mounted to said main housing and is movable from external of said storage cavity when said portable dental apparatus is in said in-use stationary state and into said storage cavity when said portable dental apparatus is in said transport state;
said plurality of dental tools include a dental drill hand piece, a syringe, a suction hand piece, and a dental curing wand;
a lid mounted to said control panel and movable to an open condition uncovering said control panel when said portable dental apparatus is in said in-use stationary state and to a closed condition covering said control panel when said portable dental apparatus is in said transport state;
control means having a foot control and a line connecting said foot control to said drive means, said foot control stored within said cavity when said portable dental apparatus is in said transport state, said control means further having additional controls mounted on said control panel and operably associated with said tools and said drive means, said additional controls being concealed when said lid is closed and said portable dental apparatus is in said transport state;
said lid is hingedly mounted atop said main housing;
said main housing includes mounted therein a compressor, a source of water, and a container for liquid waste;
said control panel includes mounted thereon amalgamate means operable to shake materials to be affixed to a tooth, said control panel further includes mounted thereon said additional controls which includes drill speed control means associated with said dental drill hand piece and said compressor, and water flow control means associated with said source of water and said syringe; and
said lid includes a lightable x-ray display means thereon.

2. The portable dental apparatus of claim 1 wherein:
said dental tool holding means includes a plurality of tool holders joined together and extending across said main housing, said dental tool holding means further includes a pair of arms joined to said holders with said arms slidably mounted to said main housing allowing said holders to be slidably moved into and out of said storage cavity.

3. The portable dental apparatus of claim 2 wherein:
said main housing includes a pair of doors hingedly mounted thereto cooperating with said lid to enclose said control panel and said storage cavity, said main housing further includes a lower forward wall and a recessed front wall with said doors vertically aligned with said lower forward wall when in the closed position and forming said storage cavity between said doors and said recessed front wall, said main housing includes a bottom wall with said lower forward wall and said recessed front wall extending upwardly therefrom and forming a storage recess.

4. A portable dental apparatus comprising:
a portable main housing having an interior;
transport means beneath said main housing operable to allow said portable dental apparatus to have an in-use stationary state and a transport state;
dental tool holding means on said main housing;
a plurality of dental tools removably mountable on said dental tool holding means;
drive means mounted within said interior operable to drive said dental tools;
connecting means connected between said drive means and said plurality of dental tools;
lid means mounted to said main housing, said lid means and said main housing forming a storage cavity to receive said plurality of dental tools and said connecting means when said portable dental apparatus is in said transport state;
said dental tool holding means is movably mounted to said main housing and is movable from external of said storage cavity when said portable dental apparatus is in said in-use stationary state and into said storage cavity when said portable dental apparatus is in said transport state;
said plurality of dental tools include a dental drill hand piece, a syringe, and a suction handpiece;

said main housing includes a control panel operably associated with said drive means and said plurality of dental tools, said lid means and further includes a lid mounted atop said control panel, said lid is movable to an open condition uncovering said control panel when said portable dental apparatus is in said in-use stationary state and to a closed condition covering said control panel when said portable dental apparatus is in said transport state;

control means having a foot control and a line connecting said foot control to said drive means, said foot control stored within said cavity when said portable dental apparatus is in said transport state, said control means further having additional controls mounted on said control panel and operably associated with said tools and said drive means, said additional controls being concealed when said lid is closed and said portable dental apparatus is in said transport state;

said drive means includes a compressor, a source of water, and a removable container for liquid waste;

said control panel includes mounted thereon amalgamate means operable to shake materials to be affixed to a tooth, said control panel further includes mounted thereon said additional controls which includes drill speed control means associated with said dental drill hand piece and said compressor, and water flow control means associated with said source of water and said syringe; and said lid includes a lightable x-ray display means thereon.

5. The portable dental apparatus of claim 4 wherein:

said dental tool holding means includes a plurality of tool holders joined together and extending across said main housing, said dental tool holding means further includes a pair of arms joined to said holders with said arms slidably mounted to said main housing allowing said holders to be slidably moved into and out of said storage cavity.

6. The portable dental apparatus of claim 5 wherein:

said main housing includes a pair of doors hingedly mounted thereto cooperating with said lid to enclose said control panel and said storage cavity, said main housing further includes a lower forward wall and a recessed front wall with said doors vertically aligned with said lower forward wall when in the closed position and forming said storage cavity between said doors and said recessed front wall, said main housing includes a bottom wall with said lower forward wall and said recessed front wall extending upwardly therefrom and forming a storage recess.

7. A portable dental apparatus comprising:

a portable main housing having an interior, said main housing including transport means therebeneath operable to allow said portable dental apparatus to have an in-use stationary state and a transport state;

dental tool holding means on said main housing, said dental tool holding means is slidably mounted to said main housing and is slidable horizontally inward from external of said housing when said portable dental apparatus is in said in-use stationary state and into said housing when said portable dental apparatus is in said transport state, said dental tool holding means includes a plurality of tool holders joined together and extending across said main housing, said dental tool holding means further includes a pair of arms joined to said holders with said arms horizontally slidably mounted to said main housing allowing said holders to be slidably moved into and out of said housing;

a plurality of dental tools removably mountable on said dental tool holding means;

drive means mounted within said interior operable to drive said dental tools;

connecting means connected between said drive means and said plurality of dental tools;

a control panel operably associated with said drive means and said plurality of dental tools, said control panel located on said main housing with said main housing sized to form a storage cavity to receive said plurality of dental tools and said connecting means when said portable dental apparatus is in said transport state;

a lid mounted to said control panel and movable to an open condition uncovering said control panel when said portable dental apparatus is in said in-use stationary state and to a closed condition covering said control panel when said portable dental apparatus is in said transport state, said lid is hingedly mounted atop said main housing; and wherein;

said main housing includes a pair of doors hingedly mounted thereto cooperating with said lid to enclose said control panel and said storage cavity, said main housing further includes a lower forward wall and a recessed front wall with said doors vertically aligned with said lower forward wall when in the closed position defining a first vertical plane with said recessed front wall defining a second vertical plane, said storage cavity formed between said first vertical plane and said second vertical plane and further between said doors and said recessed front wall, said main housing includes a bottom wall with said lower forward wall and said recessed front wall extending upwardly therefrom and forming a storage recess.

8. The portable dental apparatus of claim 21 wherein:

said control panel includes mounted thereon amalgamate means operable to shake materials to be affixed to a tooth, said control panel further includes mounted thereon additional controls which include drill speed control means and water flow control means; and, said lid includes a lightable x-ray display means thereon.

* * * * *

UNITED STATES PATENT AND TRADEMARK OFFICE
CERTIFICATE OF CORRECTION

PATENT NO. : 5,013,240

DATED : May 7, 1991

INVENTOR(S) : James R. Bailey, et al.

It is certified that error appears in the above-identified patent and that said Letters Patent is hereby corrected as shown below:

In column 3, line 59 please change "conventional i nature" to --conventional in nature--.

In column 12, line 50 please change "claim 21 to --claim 7--.

Signed and Sealed this

Twenty-second Day of September, 1992

Attest:

DOUGLAS B. COMER

*Attesting Officer*    *Acting Commissioner of Patents and Trademarks*